US00PP18839P2

(12) United States Plant Patent
Korlipara

(10) Patent No.: US PP18,839 P2
(45) Date of Patent: May 27, 2008

(54) *ECHINACEA* PLANT NAMED 'TIKI TORCH'

(50) Latin Name: *Echinacea hybrida*
Varietal Denomination: Tiki Torch

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/637,444

(22) Filed: Dec. 11, 2006

(51) Int. Cl.
*A01H 5/00* (2006.01)

(52) U.S. Cl. ..... Plt./428; Plt./263.1
(58) Field of Classification Search ..... Plt./263, Plt./428
See application file for complete search history.

*Primary Examiner*—Kent Bell
*Assistant Examiner*—S. B. McCormick-Ewoldt
(74) *Attorney, Agent, or Firm*—Klarquist Sparkman, LLP

(57) ABSTRACT

A new and distinct *Echinacea* plant named 'Tiki Torch' characterized by large, bright orange flowers, well-branched upright flower stalks, and excellent vigor.

1 Drawing Sheet

Botanical denomination: *Echinacea hybrida.*
Variety designation: 'Tiki Torch'.

The present invention relates to a new and distinct cultivar of *Echinacea* and given the cultivar name 'Tiki Torch'. *Echinacea* is in the family Asteraceae. This new cultivar originated as a third generation seedling from a planned breeding program using the parents *Echinacea paradoxa* as the seed parent and *Echinacea purpurea* 'Ruby Giant' as the pollen parent for the initial cross. The best offspring were not named but were line crossed for two generations. This selection was made from the offspring for its excellent and unique qualities.

This new *Echinacea* cultivar is distinguished by:

1. Large, bright orange flowers
2. Well-branched upright flower stalks
3. Excellent vigor This new cultivar has been reproduced only by asexual propagation (division and tissue culture). Each of the progeny exhibits identical characteristics to the new cultivar. Asexual propagation by division and tissue culture using standard micropropagation techniques with terminal and lateral shoots, as done in Canby, Oreg, shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows the flowers of *Echinacea* 'Tiki Torch' cut from a plant growing in the ground in full sun in the field in late summer in Canby, Oreg.

DETAILED PLANT DESCRIPTION

The following is a detailed description of the new *Echinacea* cultivar based on observations of a 7-months-old specimen growing in the ground in full sun under typical outdoor conditions in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart.

Plant:
- *Type.*—Herbaceous perennial.
- *Hardiness.*—USDA Zones 4 to 9.
- *Size.*—55 cm wide and 90 to 100 cm tall to top of flowers.
- *Form.*—Basal clump.
- *Vigor.*—Excellent.
- *Roots.*—Fibrous, with many downward growing and few laterals, ivory in color, Yellow White 158D, roots develop easily from cuttings from the crown.

Stem (flowering):
- *Type.*—Ascending.
- *Size.*—Grows from 90 to 100 cm tall to terminal flower and 1.3 cm wide at base.
- *Internode length.*—2 to 6.5 cm.
- *Surface texture.*—Strigose.
- *Color.*—Yellow Green 146A.

Leaf (basal and stem):
- *Type.*—Simple.
- *Shape.*—Most lanceolate, upper stem leaves ovate.
- *Arrangement.*—Basal, stem leaves alternate.
- *Blade size.*—Grows to 19.5 cm long and 5.5 cm wide.
- *Margins.*—Entire.
- *Apex.*—Acuminate.
- *Base.*—Attenuate, continuing down petiole, clasping.
- *Surface texture.*—Strigose on both sides.
- *Venation.*—Pinnate.
- *Color.*—Topside — Yellow Green 147A with the vein Yellow Green 147B. Bottom — Yellow Green 147A with the veins Yellow Green 147B.
- *Petiole description.*—Grows to 10.5 cm long and 3 mm wide if basal leaf and 3 cm long and 7 mm wide if cauline leaf, strigose, Yellow Green 147B except at base on basal leaves where Grayed Purple 187A.

Inflorescence:
- *Type.*—On long stalked terminal heads.
- *Peduncle description.*—Grows from 90 to 100 cm tall from the base of the plant to the terminal flower and can grow to 42 cm long from the top leaf to the top of a flower head; diameter growing to 12 mm wide near the flower head; strigose, branched, with one to five branches, 0 to 1 linear bract.

*Number of inflorescences.*—5.

*Number of flowering stems per plant in summer.*—1.

*Bloom time.*—Summer until frost in Canby, Oreg.

*Size.*—Grows to 11.5 cm wide and 6 cm deep as disc enlarges.

*Form.*—Ray petals held at a downward 10 to 20 degree angle, mature disc is conic.

*Immature inflorescence.*—3.3 cm wide and 2.3 cm deep, ray petals held upright and colored Yellow Green 145B tinted Greyed Orange 174C, disc is tinted Greyed Orange 176B.

*Ray florets.*—Without pistil or stamen. Shape: oblanceolate with the tip two to three toothed and cupped down, entire margins, base attenuate, ray florets sometimes overlapping. Number: 15 to 19 ray florets per head. Size: grows to 4.5 cm long, 14 mm wide. Surface texture: glabrous on both sides.

*Ray florets color.*—Topside — overall closest to Orange28A, in detail the base and edges are Orange 28A and the middle is Orange 25A with shades of Yellow Orange 22A in the veins (As the ray florets mature the lighter Orange 25A and Yellow Orange 22A dominate and the most mature ray florets dull to a color closest to Greyed Orange 163A.). Bottom side — Greyed Orange 172A on the edges and base with Greyed Orange 163B in the center maturing to Greyed Orange 163B overall.

*Disc.*—Overall shape — convex becoming conic. Overall size — 4 cm wide and becoming 3.5 cm deep with maturity. Overall color — Greyed Red 180A.

*Disc florets.*—About 240 in number, 14 mm long, each with one persistent, very stiff bract with a spiny top which gives the disc color and a base which wraps around the disc floret. Bract — 16 mm long, Greyed Purple 187A at the tip to Greyed Purple 185A below the tip and Greyed Orange 164B, base Yellow Green 146A and lighter. Corolla — 6 mm long and 1.5 mm wide, 5 lobed, Yellow Green 145C to Yellow Green 146C at the tip, glabrous. Pistil — 15 mm long, with an extruding, 2-branched stigma, spreading 3.5 mm wide, Greyed Purple 187A, style 7 mm long, White 155A, ovary 4 mm long and Yellow White 158C with Yellow Green 144C at top. Stamen — 6 mm long, anthers 3 mm long and Black 201A, filaments 3 mm long, Yellow White 158C, pollen Yellow Orange 20A.

*Phyllaries.*—In 4 leafy series, area 3.2 cm wide, lobes lanceolate in shape, reflexed, can grow to 12 mm long and 4 mm wide, Yellow Green 147B, margins strigose, tip acute.

*Bloom period.*—July through October in Canby, Oreg.

*Fragrance.*—Lovely, strong.

Seed: Average number of 24 seeds/head.

*Description.*—4 mm long and 2.5 mm wide, oval, Greyed Green 197A.

*Fertility.*—Good.

Disease and pests: *Echinacea* are susceptible to leaf miners, powdery mildew, bacterial spots, and gray mold. None of these have been observed on plants grown under commercial conditions in Canby, Oreg. No resistance is known.

COMPARISONS TO SIMILAR *ECHINACEA*

Compared to *Echinacea* 'Ruby Giant', an unpatented plant and one of the original parents in the breeding line, the new variety has orange rather than red purple flowers.

Compared to *Echinacea* 'Orange Meadowbrite'™ (aka 'Art's Pride' and U.S. Plant Pat. No. 15,090), the new variety has deeper orange ray floret color, larger flower heads, and wider ray florets. Compared to *Echinacea* 'Sunset' (U.S. Plant Pat. No. 16,424), the new variety has bright pumpkin orange flowers rather than red orange. The new variety is taller.

I claim:

1. A new and distinct *Echinacea* plant as herein illustrated and described.

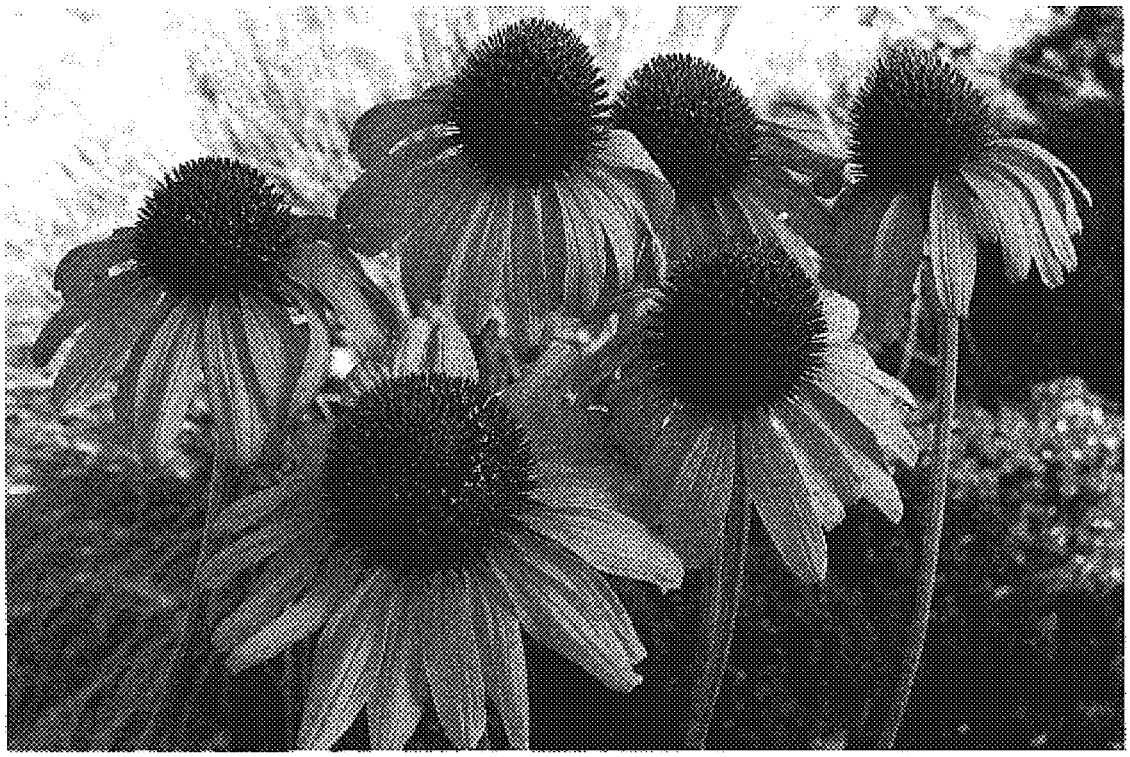

* * * * *